United States Patent [19]

Schreiber

[11] Patent Number: 4,776,339

[45] Date of Patent: Oct. 11, 1988

[54] INTERLOCK FOR OXYGEN SATURATION MONITOR ANESTHESIA APPARATUS

[75] Inventor: Joachim M. Schreiber, Harleysville, Pa.

[73] Assignee: N.A.D., Inc., Telford, Pa.

[21] Appl. No.: 22,200

[22] Filed: Mar. 5, 1987

[51] Int. Cl.$^4$ .................................................. A61B 5/00
[52] U.S. Cl. ...................................... 128/633; 128/670; 128/677
[58] Field of Search ............... 128/633, 634, 630, 670, 128/677, 667, 671

[56] References Cited

U.S. PATENT DOCUMENTS

| 3,536,062 | 10/1970 | Horn | 128/671 |
| 4,184,485 | 1/1980 | Agoston | 128/670 |
| 4,729,381 | 3/1988 | Harada et al. | 128/671 |

FOREIGN PATENT DOCUMENTS 0104771  4/1984  European Pat. Off. ............ 128/633

Primary Examiner—William E. Wayner
Attorney, Agent, or Firm—Caesar, Rivise, Bernstein, Cohen & Pokotilow, Ltd.

[57] ABSTRACT

An interlock system for use with anesthesia equipment or other apparatus for monitoring a person's arterial blood pressure and the level of oxygen saturation in the person's blood and for providing respective blood pressure and oxygen saturation signals indicative thereof. The apparatus also comprises inflatable cuff means for disposition about the upper arm of the person to provide the blood pressure signal and a probe for securement on the finger of the person to provide the oxygen saturation signal. The apparatus further comprises alarm means coupled to the cuff means and to the probe means for providing a blood pressure alarm signal in the event that the monitored blood pressure signal deviates from a predetermined value and for providing an oxygen saturation signal in the event that the value of the monitored oxygen saturation signal deviates from a predetermined value. The interlock system basically comprises control means operative when actuated to automatically respond to the inflation of the cuff means to provide a signal to the apparatus alarm means for disabling the oxygen saturation alarm if the cuff is inflated. An advisory signal is provided to indicate the disabling of the oxygen saturation alarm signal. The control means includes timer means for reenabling the oxygen saturation alarm either a first predetermined time period, e.g., five seconds, after the cuff is deflated or the inerlock deactivated and a pulse is detected, or a second, and longer, predetermined period of time, e.g., 30 seconds, after the cuff is deflated or the interlock deactivated.

12 Claims, 4 Drawing Sheets $S_aO_2$ MONITOR ARCHITECTURE $S_aO_2$/NIBP INTERLOCK FLOW CHART

INTERLOCK FOR OXYGEN SATURATION MONITOR ANESTHESIA APPARATUS

BACKGROUND OF THE INVENTION

This invention relates generally to medical equipment and more particularly to non-invasive systems for monitoring arterial oxygen saturation, pulse rate and blood pressure.

Various anesthesia systems are commercially available for delivering anesthesia gases to the patient. Some of such prior art systems, in addition to providing means for monitoring machine functions, also include monitors for non-invasive measurements of the patient's blood pressure, oxygen saturation and pulse rate. Such monitors typically include alarm devices for providing a visual and/or audible alarm in the event that the monitored parameters deviate from predetermined limits or settings.

In some anesthesia systems non-invasive monitoring of blood pressure is accomplished by utilizing an inflatable blood pressure cuff which is wrapped about the arm of the patient. The cuff is connected via a hose with leuer lock fittings to a monitor. The monitor may comprise oscillometric means for determining the patient's systolic, diastolic and mean blood pressure (mean arterial pressure).

In some anesthesia systems non-invasive measurement of arterial hemoglobin oxygen saturation and pulse rate is accomplished through the use of a pulse oximeter monitor utilizing a clip or probe arranged to be secured to the patient's finger. The clip includes spectrophotometric infrared transmission means and sensors to provide signals from which arterial hemoglobin oxygen saturation and pulse rate are calculated by the monitor.

As will be appreciated by those skilled in the art when it is desired to take a person's blood pressure while also monitoring his/her arterial hemoglobin oxygen saturation and pulse rate utilizing monitors as described above, it is the accepted practice to place the blood pressure sensing cuff on one arm of the patient and the oxygen saturation/pulse rate monitoring probe on the finger of the hand on the other arm since the inflation of the blood pressure cuff occludes or obstructs the flow of blood through the arm. Thus, if the oxygen saturation sensing probe were disposed on the finger of the arm about which the pressure cuff was inflated the flow of blood to the finger would be impeded, whereupon the oxygen saturation/ pulse rate monitor would provide a false alarm signal indicating a deviation from the pre-established limits or set points. Such a false alarm is a nuisance since it disrupts communication among operating personnel in the vicinity of the system, while also detracting from perceived urgency of actual alarm conditions.

In some cases, such as when a patient has had surgery on one arm, it is not possible nor practical to measure blood pressure on one arm and oxygen saturation on the other. Thus, if both the pressure cuff and the oxygen saturation/pulse rate probe are to be used on one arm, the need exists for an interlock system to preclude the generation of spurious or false alarms by the pulse oximeter monitor when the cuff is in place and inflated.

OBJECTS OF THE INVENTION

Accordingly, it is a general object of the instant invention to provide an interlock system which overcomes the disadvantages of the prior art.

It is a further object of the instant invention to provide an activatible interlock system for a non-invasive pulse oximeter having a finger probe and which is arranged when activated to disable the pulse oximeter alarm in the event that a non-invasive blood pressure cuff is inflated on the same arm of the patient.

It is a further object of the instant invention to provide an interlock system for a non-invasive pulse oximeter monitor having a finger probe and which disables the monitor's alarm when a non-invasive blood pressure monitoring cuff is inflated on the same arm of the patient, while reenabling the alarm a predetermined time after the cuff is deflated.

It is still a further object of this invention to provide an interlock system for a non-invasive pulse oximeter which is arranged to provide an indication of the actuation of the interlock.

SUMMARY OF THE INVENTION

These and other objects of the instant invention are achieved by providing an interlock system for use with apparatus for measuring a person's arterial blood pressure and arterial hemoglobin oxygen saturation. The apparatus comprises inflatable cuff means for disposition about the upper arm of the person to provide a first signal to the apparatus. The apparatus uses that first signal to produce a signal indicative of the person's arterial blood pressure. The apparatus also includes probe means for disposition on the finger of the person to provide a second signal to the apparatus. The second signal is used by the apparatus to produce a signal indicative of the person's arterial hemoglobin oxygen saturation. The apparatus also includes alarm means coupled to the cuff means and the probe means to provide a first alarm signal in the event that the value of the arterial hemoglobin oxygen saturation signal deviates from a preestablished value. The interlock system is actuatable, and comprises control means which when actuated is responsive to the inflation of the cuff means for providing a disable signal to the alarm means to disable the first alarm signal while the cuff means is inflated.

BRIEF DESCRIPTION OF THE DRAWINGS

Other objects and many of the attendant advantages of this invention will be readily appreciated as the same become better understood by reference to the following detailed description when considered in connection with the accompanying drawing wherein.

DETAILED DESCRIPTION OF THE PREFERRED EMBODIMENT

Figure 1:
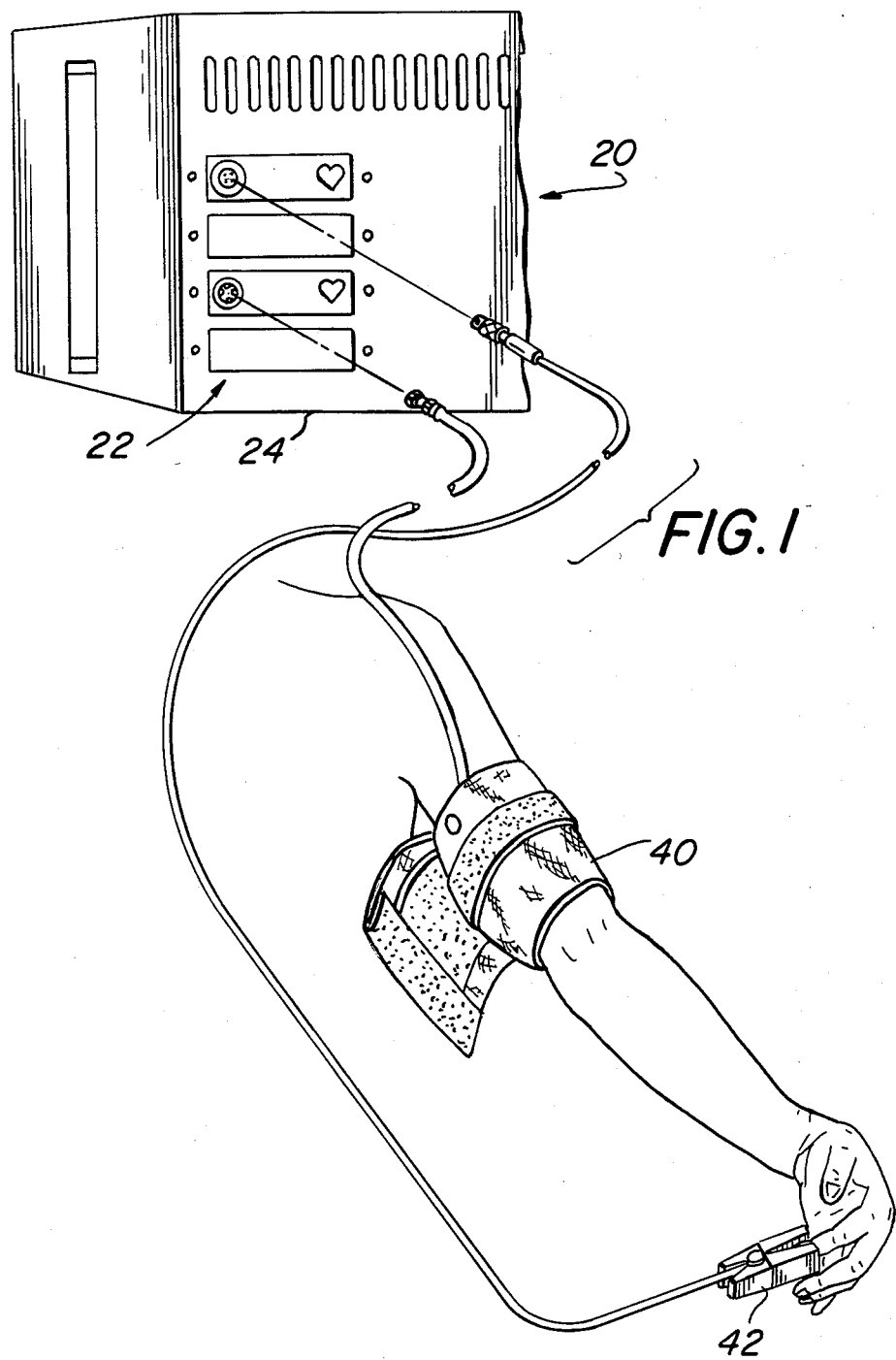
FIG. 1 is a perspective view of a portion of an anesthesia apparatus including the interlock system of the subject invention used in connection with a pulse oximeter monitor and a non-invasive blood pressure monitor and a respective probe and cuff connected thereto shown disposed on one arm of a patient.

Referring now in greater detail to the various figures of the drawings wherein like reference characters refer to like parts, there is shown at 20 in FIG. 1 an interlock system constructed in accordance with this invention. The system 20 is arranged for use with an anesthesia apparatus or system 22 having a non-invasive blood pressure monitor and a non-invasive hemoglobin oxygen saturation monitor, e.g., pulse oximeter. It should be pointed out at this junction that the interlock system 20 can be used with other equipment, not necesaarily an anesthesia apparatus, so long as the equipment includes a non-invasive blood pressure monitor and a non-invasive hemoglobin oxygen saturation monitor.

Figure 2:
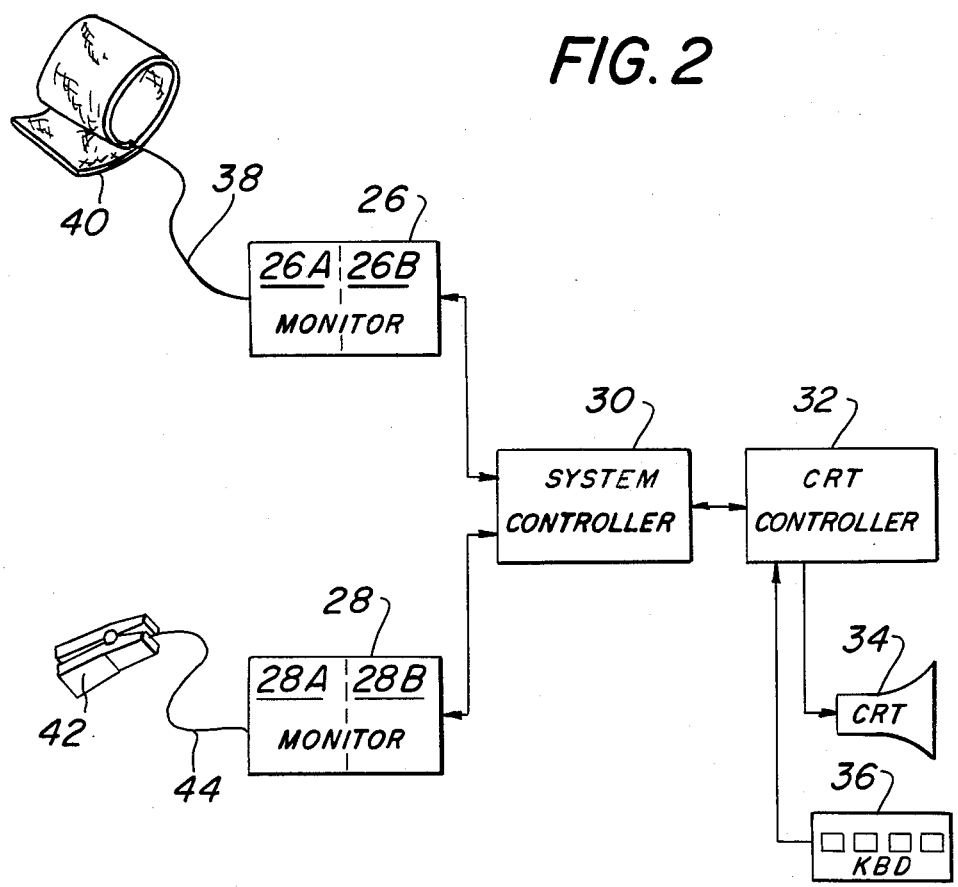
FIG. 2 is a overall block diagram of the relevant portion of the anesthesia apparatus to which the interlock system of the subject invention pertains.

The interlock system 20 and the various components of the anesthesia apparatus 22 (which will be described later) are located within a housing 24, only a portion of which is shown herein. The details of the anesthesia apparatus 22 will not be described herein. Suffice to say that, as shown in FIG. 2, the anesthesia apparatus includes, among other things not germain to this invention, a non-invasive blood pressure monitor 26, a non-invasive pulse oximeter monitor (referred to by the designation SaO2) 28, a system controller 30, a cathode ray tube controller 32, a cathode ray tube (CRT) 34, and an associated keyboard or key pad 36.

The cathode ray tube 34 serves to display various menus relating to the operation of the anesthesia apparatus and also display various monitored system or patient parameters in numerical or graphical form to expedite system usage by operating personnel. Data or instructions for operation of the apparatus are entered via the keyboard 36.

The non-invasive blood pressure monitor is connected, via a pneumatic line 38, to an inflatable blood pressure cuff 40. The cuff is arranged to be disposed about the arm of a person. A description of the cuff 42 will follow. Suffice for now to state that the cuff provides pneumatic signals, via the line 38, to the monitor 26. The monitor 26 includes two basic portions, namely a front end or a data acquisition unit 26A, and an interface/display unit 26B. The data acquisition unit 26A is a conventional device which employs oscillometric means responsive to pneumatic signals from the cuff to measure the patients'systolic, diastolic, mean blood pressure (i.e., mean arterial pressure), and pulse rate. Thus, the pressure cuff 40 does not include pressure transducers or microphones, as they are located within the data acquisition unit 26A. Those means and a microprocessor (not shown) located within the data acquisition unit 26A translate pressure oscillations sensed by the cuff 42 into meaningful blood pressure indicating electrical signals. Those signals are used by the interface/display unit 26B, as will be described later.

One particularly effective data acquisition unit 26A is sold by Colin Medical Instruments Corp. of South Plainfield, N.J. under the Model designation Nippon Colin #PC-003.

The blood pressure cuff 40 is also a conventional device and basically comprises an inflatable bag arranged to be wrapped around the upper arm of the patient, with its center of inflation located over the brachial artery. The bag is held in place by conventional hook and loop fasteners, such as those identified by the trademark Velcro. One particularly effective cuff is sold by W. A. Baum Co. of Copiague, N.Y. under the Model designation #14-410.

The cycle of operation of the non-invasive blood pressure monitor 26 is as follows. At predetermined time intervals the data acquisition unit 26A pumps up the cuff 40, via the interconnected pneumatic hose 38. Since the cuff is wrapped about the patient's arm its inflation occludes the flow of blood through the brachial artery. The pressure sensor (tranducer) in data acquisition unit 26A monitors the pressure in the cuff. At the point that the cuff pressure is equal to the blood pressure the blood begins to flow through the artery, thereby creating pressure oscillations and corresponding sounds. The pressure at this time is known as the systolic pressure and is stored in the data acquisition unit. The data acquisition unit allows the pressure in the cuff to continue to bleed down until the pressure oscillations are at a maximum value. At that time the blood pressure is known as the mean blood pressure and its value is also stored in the data acquisition unit. The data acquisition unit continues to allow the pressure in the cuff to bleed down further until the pressure pulsations begin to disappear. The pressure existing at this time is known as the diastolic pressure and is also stored by the data acquisition unit. Thereafter the cuff is completely deflated and the measurment cycle completed.

As mentioned earlier the data acquisition unit 26A provides electrical output signals to the control/interface unit 26B. To that end the output signals are provided as inputs to a serial interface (to be described later) in the unit 26B. The serial interface then provides digital data signals onto a data bus for processing to effect a display of the systolic, mean and diastolic blood pressure readings taken on the patient. In particular the readings are displayed on a LED display comprising a portion of the interface/display unit 26B.

The interface/display unit 26B is similar in construction to the interface/display unit 28B of pulse oximeter monitor 28 and the details thereof will be described later. Suffice to state now that the control/interface unit 26B, among other things, includes audible alarm means to provide an audible alarm in the event that monitored pressure is either below a selectable low limit or above a selectable high limit. The blood pressure monitor 26 can also display the automatic measurement interval. That information, plus the systolic, diastolic, mean blood pressure, cuff pressure, and pulse rate are sent by the monitor 26 to the anesthesia system's central display, e.g., CRT 34, for display to personnel using the system.

The pulse oximeter (SaO2) monitor 28 basically comprises a data acquisition module or front end 28A and an interface/display unit or module 28B. The data acquisition unit serves to non-invasively monitor both arterial hemoglobin oxygen saturation and pulse rate in response to electrical signals received from a spectrophotometric transmission sensor or probe 42. The probe (to be described later) is arranged to be mounted on the finger of a patient. Electrical signals are provided from the probe 42, via a cable 44, to a preamplifier (not shown) at the input to the data acquisition unit 28A. The preamplifier amplifies the signals from the probe and provides the amplified signals as an input to the data acquisition unit 28A. The probe 42 is a conventional device, such as sold by Nellcor, of Hayward, Calif., under the Model designation #073130, and basically includes two-powered LED light sources and a photodetector. The light sources and photodetector are mounted in a clip which is secured to the the finger of the patient so that the light sources and photodetector are on opposite sides of the finger. Under control of signals provided from the data acquisition unit 28A, via cable 44, the light sources are modulated. As arterial blood pulses between the light sources and the detector the intensity and color of the light received by the detector causes the detector to produce electrical signals indicative thereof. These signals are provided to the data acquisition unit 28A which utilizes those signals to calculate the percentage of available hemoglobin that is saturated with oxygen. The unit 28A also determines the patient's pulse rate based on those signals. The monitor then provides electrical signals indicative of the oxygen saturation and pulse rate to the interface/display unit 28B.

Figure 3:
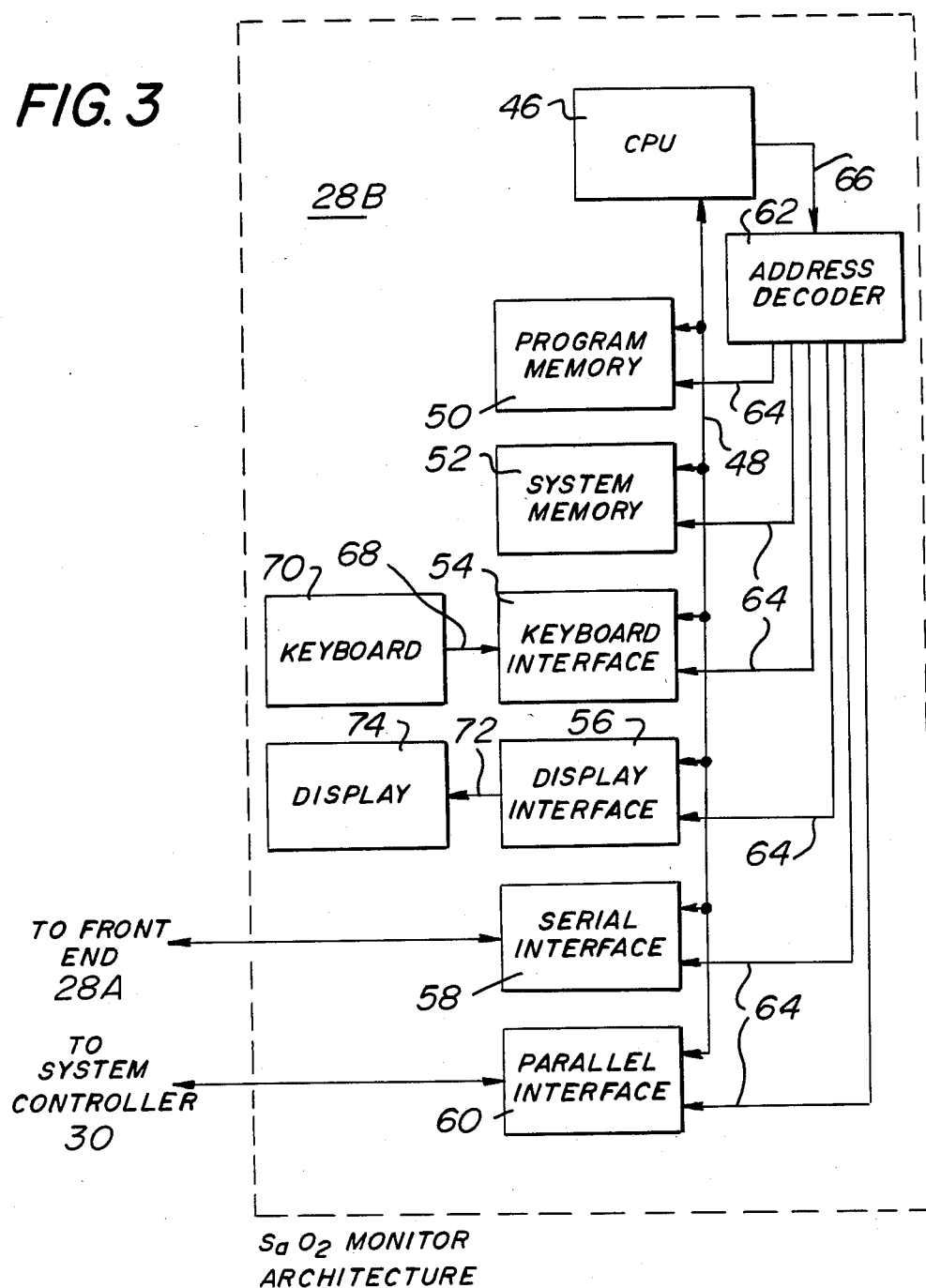
FIG. 3 is a block diagram of a portion of the pulse oximeter monitor shown in FIG. 2.

Referring now to FIG. 3 the details of the interface/display unit 28B will now be described. As can be seen that unit includes a central processing unit or microprocessor 46 connected, via a data bus 48, to a program memory (ROM) 50, a system memory (RAM) 52, a keyboard interface 54, a display interface 56, a serial interface 58, and a parallel interface 60. Addressing information for the program memory 50, system memory 52, keyboard interface 54, display interface 56, serial interface 58 and parallel interface 60 is provided to those components from an address decoder 62, via plural address lines 64. The address decoder 62 is connected to the microprocessor 46 via an address bus 66. Information to the keyboard interface is provided via line 68, from a keyboard 70. The keyboard also forms a part of the interface/display unit 28B. The output of display interface 56 is provided, via lines 72, as an input to a display 74.

The keyboard 70 is located on the housing 22 adjacent the pulse oximeter monitor 28 to enable the operator to establish operational parameters for the unit, e.g., select high and low limits for both pulse rate and oxygen saturation. The CPU or microprocessor 46 provides signals, via the serial interface 58, to the front end (data acquisition unit 28A) in accordance with instructions received from the keyboard 70, program memory 50 and system memory 52. Thus, the interface/display unit 28B instructs the data acquisition unit 28A to take readings and to also read back the data which it acquires.

The establishment of the alarm settings can also be accomplished in response to input signals from other input means than the keyboard 70.

The display portion 74 of unit 28B includes LED display means as well as the audible alarm means (not shown). These alarms, referred to hereinafter as the SaO2 alarms, provide audible signals in the event that the monitored oxygen concentration and/or pulse rate deviates from the values set. The interface/display unit 28B also includes alarm means (not shown) for providing an alarm in the event that the probe 42 becomes disconnected.

The unit 28B transmits acquired data to the system controller 30 via the parallel interface 60. Acquired data which is sent to the system controller is also transmitted to the CRT controller 32 and hence to the CRT 34 so that the data can be displayed on the face of the CRT as digital values, bar graphs or other types of graphs. The system controller 30 also includes a microprocessor for sorting and redistributing data to the various portions of the system where it is needed.

The interlock system 20 is arranged when activated to disable the pulse oximeter's low oxygen saturation (SaO2) alarm in the event that the monitor's probe 42 has to be used on the arm of a patient on which a blood pressure cuff 40 is disposed and inflated. Thus, as will be described later the interface automatically disables that alarm when the cuff is inflated, while reenabling the alarm a predetermined time after the cuff is deflated or the interface deactivated.

As mentioned earlier the system controller 30 takes inputs from the various monitors of the anesthesia apparatus to collect them for retransmission to other devices such as the CRT controller 32, a printer interface (not shown), etc. The system controller operates in conjunction with the CRT controller 32 to provide the screen menus. One such menu is a "configuration" menu which menu serves to show the status of the anesthesia system. In accordance with the preferred embodiment of this invention the configuration menu shows whether the interlock 20 has been activated or not. The interlock is activated or deactivated by appropriate keyboard 36 entry. Once activated its operational status is displayed as a message on the CRT 34.

The interlock 20 is designed to be used only if one is forced to use the same arm of the patient for monitoring blood pressure and oxygen saturation (as would be the case if one of the patient's arms is unavailable through surgery or injury).

Figure 4:
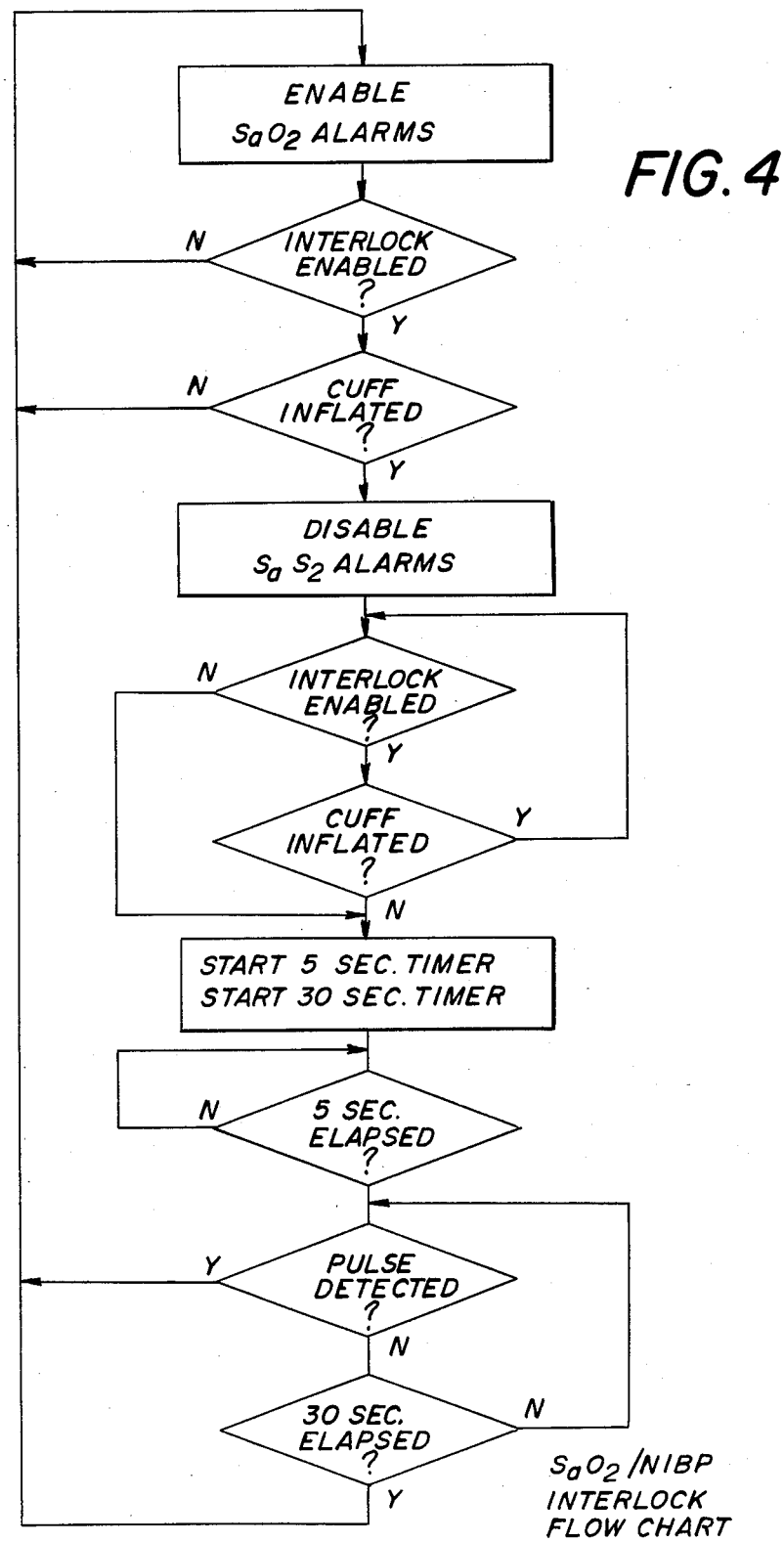
FIG. 4 is a flow chart showing the operation of the interlock system of the subject invention.

The components making up the interlock 20 are distributed throughout the system as described heretofore and define control means which will not be specifically identified herein in the interests of brevity. The functional operation of the interlock 20 will best be appreciated by reference to the flow chart of FIG. 4. Thus, as can be appreciated by reference thereto operation of the interlock system 20 is as follows: When it is desirable to activate the interlock an appropriate entry is made into the system via the keyboard 36. The CRT controller 32 then causes the CRT 34 to display the status that the interlock has been activated and also provide an interlock "enable" signal to the system controller 30. That controller in turn sends an interlock "enable" signal to the monitor's interface/display unit 28B, whereupon its SaO2 alarms will be disabled if the cuff 40 is inflated. If the cuff is not inflated the SaO2 alarms are enabled. If, the cuff is inflated the system checks to see if the interlock is still activated (enabled). If not, the system then initiates the sequence of a five second time interval and a thirty second time interval. In particular after five seconds the system determines if a pulse has been detected by the monitor 28. If so, the SaO2 alarms are enabled. If not, after thirty seconds the SaO2 alarms are enabled. If, however, the interlock is still activated the system then determines whether the cuff 40 is inflated. If the cuff is inflated the system loops until it determines that the cuff has been deflated or the interlock has been deactivated. In either case the system then initiates the five second time sequence and the thirty second time sequence, as described earlier, before reenabling the SaO2 alarms. Thus, five seconds after the cuff is sensed as being deflated or the interlock is deactivated the system determines if a pulse has been detected. If so, the SaO2 alarms are immediately enabled. If not, the alarms remain disabled until thirty seconds have elapsed, at which time the alarms are enabled.

As should be appreciated by those skilled in the art once the interlock system 20 has been activated the system will automatically reenable the oxygen saturation alarms either five seconds after the cuff is deflated (or the interlock deactivated) if a blood pressure pulse is detected or thirty seconds after the cuff is deflated (or the interlock deactivated) irrespective of whether or not a pulse is detected. This feature ensures that the SaO2 alarms will not be disabled for an unnecessarily long period of time in the interest of patient safety.

Without further elaboration the foregoing will so fully illustrate my invention that others may, by applying current or future knowledge, adopt the same for use under various conditions of service.

I claim:

1. An interlock system for use with apparatus for monitoring a person's arterial blood pressure and the person's arterial hemoglobin oxygen saturation, said apparatus comprising inflatable cuff means for disposition about the upper arm of said person to provide a first signal to said apparatus whereupon said apparatus produces a signal indicative of the person's arterial blood pressure and probe means for disposition on the finger of said person to provide a second signal to said apparatus whereupon said apparatus produces a signal indicative of the person's arterial hemoglobin oxygen saturation and alarm means coupled to said probe means for providing a first alarm signal in the event that the value of the arterial hemoglobin oxygen saturation signal deviates from a preestablished value, said interlock system being activatable and comprising control means which, when said interlock system is activated, responds to the inflation of said cuff means to provide a disable signal to said alarm means to disable said first alarm signal while said cuff means is inflated.

2. The interlock system of claim 1 wherein said control means provides an advisory signal indicating that the oxygen saturation alarm signal has been disabled.

3. The interlock system of claim 1 wherein said advisory signal is a visual signal.

4. The interlock system of claim 3 wherein said visual signal is provided by a cathode ray tube.

5. The interlock system of claim 1 wherein said control means comprises means for enabling said oxygen saturation alarm a predetermined time period after said cuff means is deflated.

6. The interlock system of claim 5 wherein said last mentioned means reenables said oxygen saturation alarm either a first predetermined time period after said cuff means is deflated if a pulse signal is detected, or a second, and longer, predetermined period of time after said cuff means is deflated.

7. The interlock system of claim 2 wherein said control means includes means for reenabling said oxygen saturation alarm a predetermined time period after said cuff means is deflated.

8. The interlock system of claim 7 wherein said last mentioed means reenables said oxygen saturation alarm either a first predetermined time period after said cuff means is deflated if a pulse signal is detected, or a second, and longer, predetermined time period after said cuff means is deflated.

9. The interlock system of claim 8 wherein said first predetermined time period is five seconds and said second predetermined time period is 30 seconds.

10. The interlock system of claim 9 wherein said oxygen saturation alarm is an audible alarm signal.

11. The interlock system of claim 1 wherein said control means comprises means for enabling said oxygen saturation alarm a predetermined time period after said interlock system is deactivated.

12. The interlock system of claim 11 wherein said last mentioned means reenables the oxygen saturation alarm either a first predetermined after said interlock system is deactivated if a pulse signal is detected, or a second, and longer, predetermined period of time after said interlock system is deactivated.

* * * * *